United States Patent
Nakajima et al.

(10) Patent No.: US 10,159,326 B2
(45) Date of Patent: Dec. 25, 2018

(54) TWO-LIQUID MIXING-TYPE AEROSOL PRODUCT

(71) Applicant: Toyo Aerosol Industry Co., Ltd., Tokyo (JP)

(72) Inventors: Yasutomo Nakajima, Tokyo (JP); Makoto Tsubouchi, Tokyo (JP); Hokuto Kamijyo, Tokyo (JP); Tomoyuki Niinomi, Tokyo (JP); Remi Ikeda, Tokyo (JP)

(73) Assignee: TOYO AEROSOL INDUSTRY CO., LTD., Tokyo (JP)

( * ) Notice: Subject to any disclaimer, the term of this patent is extended or adjusted under 35 U.S.C. 154(b) by 0 days.

(21) Appl. No.: 15/552,741

(22) PCT Filed: Feb. 23, 2016

(86) PCT No.: PCT/JP2016/055161
§ 371 (c)(1),
(2) Date: Aug. 22, 2017

(87) PCT Pub. No.: WO2016/136704
PCT Pub. Date: Sep. 1, 2016

(65) Prior Publication Data
US 2018/0035780 A1    Feb. 8, 2018

(30) Foreign Application Priority Data
Feb. 27, 2015 (JP) .................................. 2015-038111

(51) Int. Cl.
*A45D 34/04* (2006.01)
*A61Q 5/06* (2006.01)
(Continued)

(52) U.S. Cl.
CPC ................ *A45D 34/04* (2013.01); *A61K 8/02* (2013.01); *A61K 8/06* (2013.01); *A61Q 5/06* (2013.01); *A61Q 5/12* (2013.01); *B65D 83/68* (2013.01)

(58) Field of Classification Search
CPC . A45D 34/04; A61K 8/06; A61K 8/02; A61Q 5/06; A61Q 5/12; B65D 83/68
(Continued)

(56) References Cited

U.S. PATENT DOCUMENTS 6,168,335 B1 * 1/2001 Mears .................... A45D 19/02
401/118
7,036,685 B1 * 5/2006 Green .................. B65D 83/303
222/145.6
(Continued)

FOREIGN PATENT DOCUMENTS

EP         0885000 A2    12/1998
JP      2000319643 A     11/2000
(Continued)

OTHER PUBLICATIONS

International Search Report dated Apr. 5, 2016 for PCT/JP2016/055161.
(Continued)

*Primary Examiner* — Lien Ngo
(74) *Attorney, Agent, or Firm* — Lucas & Mercanti, LLP

(57) ABSTRACT

The present invention has as its object the provision of a two-liquid mixing-type aerosol product having high storage stability and being capable of easily forming a highly viscous discharge material with high functionality.

The two-liquid mixing-type aerosol product of the present invention has a double-structure container including a propellant filling space and two liquid concentrate filling spaces and having a discharging mechanism for simultaneously
(Continued)

discharging the contents in the two liquid concentrate filling spaces. The propellant filling space is filled with a propellant composed of a compressed gas. A first liquid concentrate filling space is filled with a first liquid concentrate composition, and a second liquid concentrate filling space is filled with a second liquid concentrate composition. The first liquid concentrate composition and the second liquid concentrate composition have different properties and each have a viscosity of from 1,000 to 125,000 mPa·s at a temperature of 20° C.

5 Claims, 2 Drawing Sheets

(51) Int. Cl.
    *A61Q 5/12*     (2006.01)
    *A61K 8/02*     (2006.01)
    *A61K 8/06*     (2006.01)
    *B65D 83/68*     (2006.01)

(58) Field of Classification Search
    USPC .......................... 222/94, 145.1, 145.5, 145.6
    See application file for complete search history.

(56) References Cited

U.S. PATENT DOCUMENTS

| | | | |
|---|---|---|---|
| 7,455,195 B2* | 11/2008 | Mekata | B05B 11/0043 |
| | | | 222/105 |
| 7,798,366 B2* | 9/2010 | Hoshino | B65D 83/62 |
| | | | 222/105 |
| 9,475,636 B2* | 10/2016 | Mekata | B65D 83/20 |
| 9,828,170 B2* | 11/2017 | Nomura | B65D 83/752 |
| 2003/0215416 A1* | 11/2003 | Hirano | A61K 8/046 |
| | | | 424/70.31 |
| 2007/0241133 A1 | 10/2007 | Smith et al. | |
| 2009/0108021 A1* | 4/2009 | Hansen | B65D 83/202 |
| | | | 222/1 |
| 2011/0215113 A1 | 9/2011 | Hansen et al. | |
| 2012/0126034 A1 | 5/2012 | Nolen | |
| 2013/0270294 A1* | 10/2013 | Shibata | B65D 83/48 |
| | | | 222/94 |
| 2014/0246515 A1* | 9/2014 | Nakajima | B65D 83/682 |
| | | | 239/307 |
| 2016/0128915 A1* | 5/2016 | Konno | A61Q 5/10 |
| | | | 424/62 |

FOREIGN PATENT DOCUMENTS

| | | | |
|---|---|---|---|
| JP | 2001026526 | A | 1/2001 |
| JP | 2004161292 | A | 6/2004 |
| JP | 2010069421 | A | 4/2010 |
| JP | 2010235174 | A | 10/2010 |
| JP | 2012036102 | A | 2/2012 |
| JP | 2012090966 | A | 5/2012 |
| JP | 2012-229318 | A | 11/2012 |
| JP | 5390729 | B1 | 10/2013 |
| JP | 2014237621 | A | 12/2014 |
| JP | 2015013836 | A | 1/2015 |
| WO | 2014/208735 | A1 | 12/2014 |

OTHER PUBLICATIONS

Extended European Search Report dated Jan. 30, 2018 from corresponding European Application No. 16755448.4.
Office Action dated Apr. 6, 2018 from U.S. Appl. No. 15/552,711.
Extended European Search Report dated Jan. 30, 2018 from corresponding European Application No. 16755447.6.
International Search Report dated Apr. 5, 2016 for PCT/JP2016/055160 and English translation.

\* cited by examiner

TWO-LIQUID MIXING-TYPE AEROSOL PRODUCT

CROSS REFERENCE TO RELATED APPLICATION

This Application is a 371 of PCT/JP2016/055161 filed on Feb. 23, 2016 which, in turn, claimed the priority of Japanese PCT Patent Application No. 2015-038111 filed Feb. 27, 2015, both applications are incorporated herein by reference.

TECHNICAL FIELD

The present invention relates to two-liquid mixing-type aerosol products, and in particular, to a two-liquid mixing-type aerosol product that delivers a highly viscous discharge material with high functionality.

BACKGROUND ART

There are liquid cosmetic formulations having a high viscosity. Liquid cosmetic formulations having a high viscosity have various properties. Specific examples of such liquid cosmetic formulations include creamy compositions, jelly compositions and gel compositions. Examples of these compositions include a water-based liquid composition containing a water-soluble component in a medium composed of water, an oil-based liquid composition containing an oil-soluble component in a medium composed of a liquid oil or fat immiscible with water, and a mixture of these compositions (specifically composed of a water-based liquid composition and an oil-based liquid composition and provided as an oil-in-water or water-in-oil emulsion composition by the action of a surfactant). These compositions contain, as an active ingredient, for example, an oxidizing agent component, a reducing agent component, an alkaline component, or an acidic component.

In application of highly viscous liquid cosmetic formulations, two liquid cosmetic formulations having different properties may be used in combination.

Specifically, a curly hair straightening agent is a mixture of a highly viscous liquid cosmetic formulation containing, as an active ingredient, a reducing agent such as thioglycolic acid or cysteine and a highly viscous liquid cosmetic formulation containing, as an active ingredient, an oxidizing agent such as sodium bromate or hydrogen peroxide. A hair dye is a mixture of a highly viscous liquid cosmetic formulation containing, as an active ingredient, an alkaline agent such as an oxidation dye and a highly viscous liquid cosmetic formulation containing, as an active ingredient, an oxidizing agent such as hydrogen peroxide.

When such a curly hair straightening agent and such a hair dye are used, the intended effects (specifically, a hair dyeing effect and a curly hair straightening effect) are obtained by causing two liquid cosmetic formulations separately placed in their respective containers to react at an application site (specifically, hair). Thus, two liquid cosmetic formulations cannot be mixed in advance.

In addition, there is known a technique for improving the hair styling effect by mixing two highly viscous hair styling cosmetic formulations having different properties with the hands before use. Specifically, for example, a jelly-type hair styling cosmetic formulation that offers strong setting power and provides glossy hair and a wax-type hair styling cosmetic formulation with which hair end movement and hair bundles can be created freely and the hair can be reset are used in combination.

In the combined use of these two hair styling cosmetic formulations, these two hair styling cosmetic formulations are individually filled in their respective containers hermetically sealed with lids, such as tube-type containers or cup-type containers, and thus there is the need to perform a burdensome process of mixing the high viscous hair styling cosmetic formulations taken from the respective containers. In addition, there is another problem in that sufficient storage stability may not be obtained over a long period of time because the hair styling cosmetic formulations in the containers are exposed to the air in each application.

Therefore, the inventors of the present invention have studies the feasibility of filling an aerosol container with a mixture of two highly viscous liquid cosmetic formulations.

However, when two highly viscous liquid cosmetic formulations are mixed, there is a problem in that desired functions (effects) are not obtained because each liquid cosmetic formulation has a small degree of freedom in formulation design from the viewpoint of, for example, formulation stability of active ingredients and formulation stability of a base.

Specifically, there is a severe restriction on the formulation design of each liquid cosmetic formulation, for example, in combining the jelly-type hair styling cosmetic formulation and the wax-type hair styling cosmetic formulation described above and in combining a water-based hair treatment liquid cosmetic formulation with a high viscosity containing, for example, a hair protecting and repairing component and an antistatic component, which are water-soluble components, and an oil-based hair treatment liquid cosmetic formulation with a high viscosity containing, for example, a hair-texture improving component, which is an oil-soluble component.

CITATION LIST

Patent Literature

Patent Literature 1: Japanese Patent Application Laid-Open No. 2001-26526
Patent Literature 2: Japanese Patent Application Laid-Open No. 2012-036102

SUMMARY OF INVENTION

Technical Problem

The present invention has been made in view of the foregoing circumstances and has as its object the provision of a two-liquid mixing-type aerosol product of an aerosol dispenser having high storage stability and being capable of easily forming a highly viscous discharge material with high functionality.

Solution to Problem

A two-liquid mixing-type aerosol product of the present invention has a double-structure container including a propellant filling space and two independent liquid concentrate filling spaces and having a discharging mechanism for simultaneously discharging contents filled in the two liquid concentrate filling spaces, the propellant filling space in the double-structure container is filled with a propellant composed of a compressed gas, a first liquid concentrate filling space in the double-structure container is filled with a first liquid concentrate composition, and a second liquid concentrate filling space in the double-structure container is filled with a second liquid concentrate composition, the first liquid concentrate composition and the second liquid concentrate composition have different properties, and the first liquid concentrate composition and the second liquid concentrate composition each have a viscosity of from 1,000 to 125,000 mPa·s at a temperature of 20° C.

In the two-liquid mixing-type aerosol product of the present invention, the first liquid concentrate composition may preferably be composed of a water-based liquid composition containing a water-soluble component in a medium composed of water, and the second liquid concentrate composition may preferably be composed of an oil-based liquid composition containing an oil-soluble component in a medium composed of a liquid oil or fat immiscible with water.

In the two-liquid mixing-type aerosol product of the present invention, the first liquid concentrate composition may preferably be composed of an oil-in-water emulsion composition, and the second liquid concentrate composition may preferably be composed of a water-in-oil emulsion composition.

In the two-liquid mixing-type aerosol product of the present invention, the first liquid concentrate composition may preferably be composed of an alkaline liquid composition containing an alkaline component, and the second liquid concentrate composition may preferably be composed of an acidic liquid composition containing an acidic component.

In the two-liquid mixing-type aerosol product of the present invention, the first liquid concentrate composition may preferably be composed of a liquid reducing agent composition containing a reducing agent, and the second liquid concentrate composition may preferably be composed of an liquid oxidizing agent composition containing an oxidizing agent.

In the two-liquid mixing-type aerosol product of the present invention, the mixing ratio of the first liquid concentrate composition to the second liquid concentrate composition (the mass of the first liquid concentrate composition: the mass of the second liquid concentrate composition) discharged from the discharging mechanism may preferably be from 0.8:1.2 to 1.2:0.8.

Advantageous Effects of Invention

The two-liquid mixing-type aerosol product of the present invention has a double-structure container including a discharging mechanism for simultaneously discharging the contents filled in two liquid concentrate filling spaces. One of the two liquid concentrate filling spaces is filled with a first liquid concentrate composition having a particular viscosity, whereas the other is filled with a second liquid concentrate composition having a particular viscosity. Thus, the first liquid concentrate composition and the second liquid concentrate composition both have a large degree of freedom in formulation design, and high formulation stability is obtained. Even when the first liquid concentrate composition and the second liquid concentrate composition have a high viscosity, the first liquid concentrate composition and the second liquid concentrate composition can always be discharged at a constant quantitative ratio. Moreover, the long-term storage stability can be obtained because neither the first liquid concentrate composition nor the second liquid concentrate composition is exposed to the air outside the container during application.

The two-liquid mixing-type aerosol product of the present invention has high storage stability and can easily form a highly viscous discharge material with high functionality.

DESCRIPTION OF EMBODIMENTS

Figure 1:
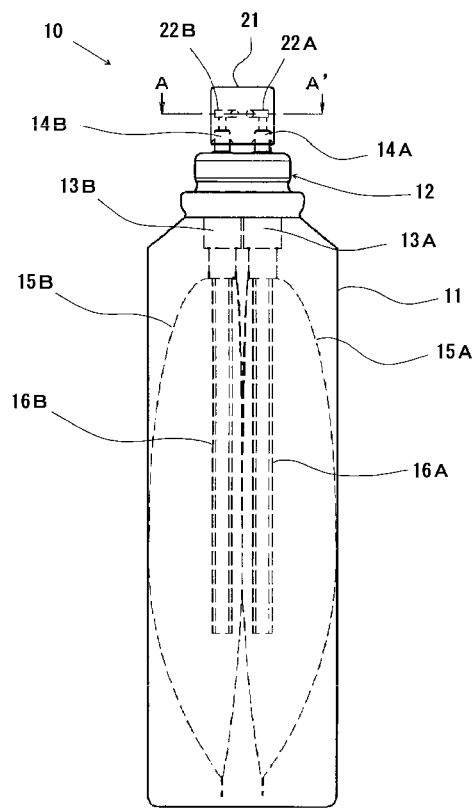
FIG. 1 is an explanatory view illustrating an example structure of a double-structure container used for a two-liquid mixing-type aerosol product of the present invention.

A two-liquid mixing-type aerosol product of the present invention has a double-structure container including a propellant filling space and two independent liquid concentrate filling spaces and having a discharging mechanism for simultaneously discharging the contents filled in these two liquid concentrate filling spaces. In this double-structure container, the propellant filling space is filled with a propellant composed of a compressed gas, a first liquid concentrate filling space is filled with a first liquid concentrate composition, and a second liquid concentrate filling space is filled with a second liquid concentrate composition.

In the two-liquid mixing-type aerosol product of the present invention, the first liquid concentrate composition and the second liquid concentrate composition simultaneously discharged from the first liquid concentrate filling space and the second liquid concentrate filling space, respectively, are used in combination to form a high viscous composition having high functionality.

In the two-liquid mixing-type aerosol product of the present invention, the first liquid concentrate composition and the second liquid concentrate composition have different properties.

Specific suitable examples of the two-liquid mixing-type aerosol product of the present invention include the examples (1) to (4) described below.

(1) In a first specific example, the first liquid concentrate composition is composed of a water-based composition containing a water-soluble component in a medium composed of water, and the second liquid concentrate composition is composed of an oil-based composition containing an oil-soluble component in a medium composed of a liquid oil or fat immiscible with water.

(2) In a second specific example, the first liquid concentrate composition is composed of an oil-in-water emulsion composition, and the second liquid concentrate composition is composed of a water-in-oil emulsion composition.

(3) In a third specific example, the first liquid concentrate composition is composed of an alkaline liquid composition containing an alkaline component, and the second liquid concentrate composition is composed of an acidic liquid composition containing an acidic component.

(4) In a fourth specific example, the first liquid concentrate composition is composed of a liquid reducing agent composition containing a reducing agent component, and the second liquid concentrate composition is composed of an liquid oxidizing agent composition containing an oxidizing agent component.

Specific examples of the combination of the first liquid concentrate composition and the second liquid concentrate composition in the above-described examples (1) to (4) will be described below.

Specific examples of the two-liquid mixing-type aerosol product of the present invention in which the first liquid concentrate composition is composed of a water-based composition and the second liquid concentrate composition is composed of an oil-based composition include the examples (1-1) to (1-4) described below.

(1-1) Two-Liquid Mixing-Type Aerosol Product for Use as Beauty Agent

First liquid concentrate composition (water-based composition): a water-based liquid cosmetic formulation for whitening beauty lotions that contains vitamin C as a water-soluble component Second liquid concentrate composition (oil-based composition): a liquid cosmetic formulation for anti-aging beauty lotions that contains vitamin E as an oil-soluble component (1-2) Two-Liquid Mixing-Type Aerosol Product for Use as Hair Treatment Agent First liquid concentrate composition (water-based composition): a water-based hair treatment liquid cosmetic formulation that contains an antistatic agent and a hair protecting and repairing agent as water-soluble components Second liquid concentrate composition (oil-based composition): an oil-based hair treatment liquid cosmetic formulation that contains a hair-texture improving agent (specifically, for example, an ester oil and silicone) as an oil-soluble component (1-3) Two-Liquid Mixing-Type Aerosol Product for Use as Sunscreen First liquid concentrate composition (water-based composition): a water-based sunscreen liquid cosmetic formulation that contains a water-soluble ultraviolet absorbing agent as a water-soluble component Second liquid concentrate composition (oil-based composition): an oil-based sunscreen liquid cosmetic formulation that contains an oil-soluble ultraviolet absorbing agent as an oil-soluble component (1-4) Two-Liquid Mixing-Type Aerosol Product for Use as Cleansing Facial Wash First liquid concentrate composition (water-based composition): a liquid cosmetic formulation for facial wash Second liquid concentrate composition (oil-based composition): a liquid cosmetic formulation for cleansing Specific examples of the two-liquid mixing-type aerosol product of the present invention in which the first liquid concentrate composition is composed of an oil-in-water emulsion composition and the second liquid concentrate composition is composed of a water-in-oil emulsion composition include the examples (2-1) to (2-5) described below.

(2-1) Two-Liquid Mixing-Type Aerosol Product for Use as Beauty Agent

First liquid concentrate composition (oil-in-water emulsion composition): a cosmetic formulation for beauty jellies Second liquid concentrate composition (water-in-oil emulsion composition): a cosmetic formulation for beauty creams (2-2) Two-Liquid Mixing-Type Aerosol Product for Use as Makeup Base First liquid concentrate composition (oil-in-water emulsion composition): a liquid cosmetic formulation for cosmetic lotions Second liquid concentrate composition (water-in-oil emulsion composition): a liquid cosmetic formulation for milky lotions (2-3) Two-Liquid Mixing-Type Aerosol Product for Use as Sunscreen First liquid concentrate composition (oil-in-water emulsion composition): a liquid cosmetic formulation for cooling lotions Second liquid concentrate composition (water-in-oil emulsion composition): a sunscreen liquid cosmetic formulation (2-4) Two-Liquid Mixing-Type Aerosol Product for Use as Hair Sunscreen First liquid concentrate composition (oil-in-water emulsion composition): a hair styling liquid cosmetic formulation Second liquid concentrate composition (water-in-oil emulsion composition): a sunscreen liquid cosmetic formulation (2-5) Two-Liquid Mixing-Type Aerosol Product for Use as Liquid Foundation First liquid concentrate composition (oil-in-water emulsion composition): a liquid cosmetic formulation for beauty lotions Second liquid concentrate composition (water-in-oil emulsion composition): a liquid cosmetic formulation for liquid foundations Specific examples of the two-liquid mixing-type aerosol product of the present invention in which the first liquid concentrate composition is composed of an alkaline composition and the second liquid concentrate composition is composed of an acidic composition include the example (3-1) described below.

(3-1) Two-Liquid Mixing-Type Aerosol Product for Use as Hair Dye

First liquid concentrate composition (alkaline composition): an alkaline liquid cosmetic formulation containing an alkaline agent such as an oxidation dye Second liquid concentrate composition (acidic composition): an acidic liquid cosmetic formulation containing an oxidizing agent such as hydrogen peroxide Specific examples of the two-liquid mixing-type aerosol product of the present invention in which the first liquid concentrate composition is composed of a reducing agent composition and the second liquid concentrate composition is composed of an oxidizing agent composition include the example (4-1) described below.

(4-1) Two-Liquid Mixing-Type Aerosol Product for Use as Curly Hair Straightening Agent First liquid concentrate composition (reducing agent composition): a liquid cosmetic formulation containing a reducing agent such as thioglycolic acid and cysteine Second liquid concentrate composition (oxidizing agent composition): a liquid cosmetic formulation containing an oxidizing agent such as sodium bromate and hydrogen peroxide The two-liquid mixing-type aerosol product of the present invention is not limited to the examples (1) to (4) described above, and other examples may be employed. Other specific examples include the examples (5-1) to (5-8) described below.

As used herein, the "active ingredient" is not necessarily an active ingredient associated with the intended use of the two-liquid mixing-type aerosol product and may be, for example, an auxiliary for a main active ingredient, or a secondary active ingredient.

(5-1) Two-Liquid Mixing-Type Aerosol Product for Use as Hair Styling Agent

First liquid concentrate composition: a wax-type hair styling cosmetic formulation Second liquid concentrate composition: a jelly-type hair styling cosmetic formulation (5-2) Two-Liquid Mixing-Type Aerosol Product for Use as Whitening Beauty Agent First liquid concentrate composition: a liquid cosmetic formulation for cooling lotions that is composed of an alcohol jelly composition Second liquid concentrate composition: a liquid cosmetic formulation for whitening beauty lotions (5-3) Two-Liquid Mixing-Type Aerosol Product for Use as Beauty Agent First liquid concentrate composition: a liquid cosmetic formulation for warming beauty lotions that contains a warming component such as capsaicin as an active ingredient Second liquid concentrate composition: a liquid cosmetic formulation for cooling beauty lotions that contains a cooling component such as menthol and menthyl lactate as active ingredients (5-4) Two-Liquid Mixing-Type Aerosol Product for Use as Beauty Agent First liquid concentrate composition: a liquid cosmetic formulation for whitening beauty lotions that contains vitamin C as an active ingredient Second liquid concentrate composition: a liquid cosmetic formulation for acne treatment beauty lotions that contains salicylic acid or glycolic acid as an active ingredient (5-5) Two-Liquid Mixing-Type Aerosol Product for Use as Beauty Agent First liquid concentrate composition: a liquid cosmetic formulation for beauty lotions that contains an astringent component such as ethanol and menthol as an active ingredient Second liquid concentrate composition: a liquid cosmetic formulation for acne treatment beauty lotions that contains salicylic acid or glycolic acid as an active ingredient (5-6) Two-Liquid Mixing-Type Aerosol Product for Use as Facial Mask First liquid concentrate composition: a liquid cosmetic formulation for mud facial masks that contains kaolin, ghassoul, white clay, montmorillonite and the like as active ingredients Second liquid concentrate composition: a liquid cosmetic formulation for whitening beauty lotions that contains vitamin C as an active ingredient (5-7) Two-Liquid Mixing-Type Aerosol Product for Use as Hair Styling Agent First liquid concentrate composition: a wax-type hair styling cosmetic formulation Second liquid concentrate composition: a hair treatment liquid cosmetic formulation (5-8) Two-Liquid Mixing-Type Aerosol Product for Use as Depilatory Agent First liquid concentrate composition: a liquid cosmetic formulation for hair removal that contains a thioglycolic acid salt as an active ingredient Second liquid concentrate composition: a liquid cosmetic formulation for moisturization First Liquid Concentrate Composition:

The viscosity of the first liquid concentrate composition at a temperature of 20° C. is 1,000 to 125,000 mPa·s, preferably 1,000 to 50,000 mPa·s, more preferably 10,000 to 25,000 mPa·s.

If the viscosity of the first liquid concentrate composition is too high, it is difficult to discharge the first liquid concentrate composition. In addition, the first liquid concentrate composition may not be discharged in a desired amount associated with the amount of the second liquid concentrate composition discharged.

If the viscosity of the first liquid concentrate composition is too low, dripping may occur at an application site. In addition, the first liquid concentrate composition may not be discharged in a desired amount associated with the amount of the second liquid concentrate composition discharged.

The constituents of the first liquid concentrate composition are appropriately set according to, for example, the intended use of the two-liquid mixing-type aerosol product.

Specifically, for example, when the two-liquid mixing-type aerosol product is used as the hair treatment agent illustrated above in (1-2), the first liquid concentrate composition (water-based composition) is a highly viscous liquid containing water-soluble components in a medium composed of water. In other words, the first liquid concentrate composition contains water (specifically, for example, purified water) and water-soluble components (specifically, for example, an antistatic component such as behentrimonium chloride and a hair protecting and repairing component such as hydrolyzed collagen or keratin) as essential components. As is apparent from Example 1, the first liquid concentrate composition may contain an optional component (specifically, for example, a viscosity modifier, a preservative, and a flavor) in addition to water and a water-soluble component, which are essential components.

When the two-liquid mixing-type aerosol product is used as the hair styling agent illustrated above in (5-1), the first liquid concentrate composition is a highly viscous liquid (wax) composed of a water-in-oil emulsion composition. As is apparent from Example 2, the first liquid concentrate composition may contain an optional component (specifically, a preservative and the like) in addition to water and an oil or fat component, which are essential components.

Second Liquid Concentrate Composition:

The viscosity of the second liquid concentrate composition at a temperature of 20° C. is 1,000 to 125,000 mPa·s, preferably 1,000 to 50,000 mPa·s, more preferably 10,000 to 25,000 mPa·s.

If the viscosity of the second liquid concentrate composition is too high, it is difficult to discharge the second liquid concentrate composition. In addition, the second liquid concentrate composition may not be discharged in a desired amount associated with the amount of the first liquid concentrate composition discharged.

If the viscosity of the second liquid concentrate composition is too low, dripping may occur at an application site. In addition, the second liquid concentrate composition may not be discharged in a desired amount associated with the amount of the first liquid concentrate composition discharged.

The constituents of the second liquid concentrate composition are appropriately set according to, for example, the intended use of the two-liquid mixing-type aerosol product.

Specifically, for example, when the two-liquid mixing-type aerosol product is used as the hair treatment agent illustrated above in (1-2), the second liquid concentrate composition (oil-based composition) is a highly viscous liquid containing an oil-soluble component in a medium composed of a liquid oil or fat immiscible with water. In other words, the second liquid concentrate composition contains a liquid oil or fat (specifically, for example, light liquid isoparaffin) and an oil-soluble component (specifically, for example, jojoba oil and olive oil) as essential components. As is apparent from Example 1, the second liquid concentrate composition may contain an optional component (specifically, for example, a viscosity modifier) in addition to a liquid oil or fat and an oil-soluble component, which are essential components.

When the two-liquid mixing-type aerosol product is used as the hair styling agent illustrated above in (5-1), the second liquid concentrate composition is a highly viscous liquid (jelly) containing water and a viscosity modifier. As is apparent from Example 2, the second liquid concentrate composition may contain an optional component (specifically, a preservative and the like) in addition to water and a viscosity modifier, which are essential components.

Propellant:

A compressed gas is used as a propellant.

Examples of the compressed gas include nitrous oxide gas, nitrogen gas, carbon dioxide gas and a mixture of these gases.

This propellant is not discharged from the propellant filling space into the outside of the double-structure container along with simultaneous discharge of the first liquid concentrate composition and the second liquid concentrate composition.

The propellant may preferably be enclosed such that the pressure applied when the double-structure container is filled with the propellant is 0.3 to 1.2 MPa at 25° C.

If the pressure applied when the double-structure container is filled with the propellant (product inner pressure) is too high or too low, in both cases, the contents may not be sprayed in favorable conditions.

Double-Structure Container:

The double-structure container of the two-liquid mixing-type aerosol product of the present invention includes a propellant filling space to be filled with a propellant, a first liquid concentrate filling space to be filled with a first liquid concentrate composition, and a second liquid concentrate filling space to be filled with a second liquid concentrate composition. The double-structure container further includes a discharging mechanism for simultaneously discharging the first liquid concentrate composition and the second liquid concentrate composition from the first liquid concentrate filling space and the second liquid concentrate filling space, respectively.

Specific examples of the double-structure container according to the present invention include two containers, for example, illustrated in FIGS. 1 to 3 and described below.

FIG. 1 is an explanatory view illustrating an example structure of the double-structure container used for the two-liquid mixing-type aerosol product of the present invention. FIG. 2 is a sectional view illustrating a cross section taken along A-A' in FIG. 1.

This double-structure container 10 includes a pressure resistant container 11 made of metal and provided with an aerosol valve 12. The pressure resistant container 11 is provided thereinside with a first inner bag 15A that is formed of, for example, an aluminum laminated film and that defines a first liquid concentrate filling space to be filled with the first liquid concentrate composition, and a second inner bag 15B that is formed of, for example, an aluminum laminated film and that defines a second liquid concentrate filling space to be filled with the second liquid concentrate composition. In the pressure resistant container 11, a propellant filling space to be filled with the propellant is formed from a gap defined by the pressure resistant container 11, the first inner bag 15A, and the second inner bag 15B. The aerosol valve 12 is provided with a first stem 14A and a second stem 14B each having a stem pas sage inside. The first stem 14A and the second stem 14B are disposed to be movable up and down inside a first housing 13A and a second housing 13B, respectively. A common actuator 21 is disposed on the upper ends of the first stem 14A and the second stem 14B.

In the example illustrated in the figure, a reference character 16A denotes a first dip tube in communication with the stem passage in the first stem 14A at the lower end of the first housing 13A. The first dip tube 16A extends inside the first inner bag 15A toward the bottom of the pressure resistant container 11. A reference character 16B denotes a second dip tube in communication with the stem passage in the second stem 14B at the lower end of the second housing 13B. The second dip tube 16B extends inside the second inner bag 15B toward the bottom of the pressure resistant container 11.

In FIG. 1, the components located inside the pressure resistant container 11 and the actuator 21 are drawn with broken lines.

The common actuator 21 contains a first actuator passage 22A in communication with the stem passage in the first stem 14A, a second actuator passage 22B in communication with the stem passage in the second stem 14B, and a discharge space 23 in communication with, at its end, the first actuator passage 22A and the second actuator passage 22B and forming, at its another end, a discharge port 24.

The actuator 21 common to the first stem 14A for the first inner bag 15A and the second stem 14B for the second inner bag 15B is provided accordingly so as to form the discharging mechanism for simultaneously discharging the first liquid concentrate composition filled in the first inner bag 15A and the second liquid concentrate composition filled in the second inner bag 15B from the first inner bag 15A and the second inner bag 15B, respectively.

In the double-structure container 10 having such a structure, the first inner bag 15A is filled with the first liquid concentrate composition, the second inner bag 15B is filled with the second liquid concentrate composition, and the propellant filling space is filled with a propellant. The inside of the pressure resistant container 11 is always pressurized with the propellant accordingly. Therefore, when the actuator 21 is actuated (depressed), the pressure of the propellant shrinks the first inner bag 15A and the second inner bag 15B, which causes the first liquid concentrate composition and the second liquid concentrate composition to be discharged simultaneously from the first inner bag 15A and the second inner bag 15B, respectively. As a result, the first liquid concentrate composition and the second liquid concentrate composition are discharged from the discharge port 24 of the actuator 21.

Specifically, while the actuator 21 is not actuated or depressed in the double-structure container 10 filled with the first liquid concentrate composition, the second liquid concentrate composition, and the propellant, the first stem 14A and the second stem 14B are being pushed up to block the stem passage in the first stem 14A and the stem passage in the second stem 14B from the inside of the pressure resistant container 11. While the actuator 21 is actuated or depressed, the first stem 14A and the second stem 14B are pushed down, so that the stem passage in the first stem 14A and the stem passage in the second stem 14B simultaneously communicate with the inside of the pressure resistant container 11. The first liquid concentrate composition in the first inner bag 15A and the second liquid concentrate composition in the second inner bag 15B are discharged simultaneously through the fluid passages formed by the first dip tube 16A and the second dip tube 16B, respectively. The first liquid concentrate composition and the second liquid concentrate composition thus simultaneously discharged reach the discharge space 23 through the stem passage in the first stem 14A and the stem passage in the second stem 14B and through the first actuator passage 22A and the second actuator passage 22B, respectively. The first liquid concentrate composition and the second liquid concentrate composition are discharged from the discharge port 24 without being mixed during passage through the discharge space 23. The first liquid concentrate composition and the second liquid concentrate composition discharged from the discharge port 24 are applied to an application site after mixed on the palm or the like with, for example, the fingers if necessary.

Figure 3:
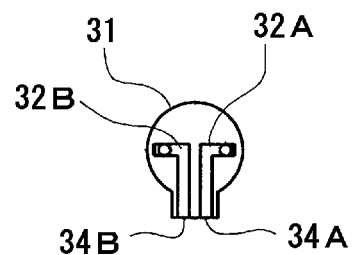
FIG. 3 is an explanatory view illustrating another example structure of a double-structure container used for a two-liquid mixing-type aerosol product of the present invention.

FIG. 3 is an explanatory view illustrating another example structure of a double-structure container used for the two-liquid mixing-type aerosol product of the present invention. Specifically, FIG. 3 is an explanatory sectional view illustrating the structure of an actuator in accordance with the double-structure container.

Figure 2:
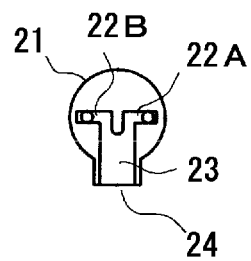
FIG. 2 is a sectional view illustrating a cross section taken along A-A' in FIG. 1.

This double-structure container has the same structure as that of the double-structure container 10 in accordance with FIG. 1 and FIG. 2 except that the actuator 21 is replaced by an actuator 31 having two discharge ports (specifically, a first discharge port 34A and a second discharge port 34B) and the first liquid concentrate composition and the second liquid concentrate composition are separately discharged from these two discharge ports, respectively.

In other words, the double-structure container in accordance with FIG. 3 includes the actuator 31 and a pressure resistant container having the same structure as that of the pressure resistant container 11 in the double-structure container 10 in accordance with FIG. 1 and FIG. 2.

The actuator 31 is provided with a first actuator passage 32A in communication with, at one end, the stem passage in the first stem and forming a first discharge port 34A at another end, and a second actuator passage 32B in communication with, at one end, the stem passage in the second stem and forming a second discharge port 34B at another end.

The actuator 31 is an actuator common to the first stem and the second stem and is disposed at the upper ends of the first stem and the second stem, like the actuator 21 in the double-structure container 10 in accordance with FIG. 1 and FIG. 2.

While the actuator 31 is actuated or depressed in the double-structure container having such a structure and filled with the first liquid concentrate composition, the second liquid concentrate composition, and the propellant, the first liquid concentrate composition in the first inner bag and the second liquid concentrate composition in the second inner bag are discharged simultaneously. The first liquid concentrate composition is discharged from the first discharge port 34A through the stem passage in the first stem in the aerosol valve and through the first actuator passage 32A, whereas the second liquid concentrate composition is discharged from the second discharge port 34B through the stem passage in the second stem in the aerosol valve and through the second actuator passage 32B. The first liquid concentrate composition and the second liquid concentrate composition discharged from the first discharge port 34A and the second discharge port 34B, respectively, are applied to an application site after mixed on the palm or the like with, for example, the fingers if necessary.

In the double-structure container having the structure described above, the discharging mechanism enables the first liquid concentrate composition filled in the first liquid concentrate filling space and the second liquid concentrate composition filled in the second liquid concentrate filling space to be discharged simultaneously. The discharging mechanism further enables the amount of the first liquid concentrate composition discharged from the first liquid concentrate filling space and the amount of the second liquid concentrate composition discharged from the second liquid concentrate filling space to be controlled at an appropriate quantitative ratio, specifically, so as to be substantially the same.

In the two-liquid mixing-type aerosol product of the present invention, the mixing ratio of the first liquid concentrate composition discharged from the first liquid concentrate filling space to the second liquid concentrate composition discharged from the second liquid concentrate filling space (the mass of the first liquid concentrate composition: the mass of the second liquid concentrate composition) may preferably be from 0.8:1.2 to 1.2:0.8.

In other words, the amount of the first liquid concentrate composition discharged from the first liquid concentrate filling space and the amount of the second liquid concentrate composition discharged from the second liquid concentrate filling space each may preferably fall within a range of ±20% of the mean of the amounts of the first liquid concentrate composition discharged and the second liquid concentrate composition discharged.

The mixing ratio (the mass of the first liquid concentrate composition: the mass of the second liquid concentrate composition) can be controlled within the above-described range by setting, for example, the viscosity of the first liquid concentrate composition at a temperature of 20° C. to 1,000 to 125,000 mPa·s, and the viscosity of the second liquid concentrate composition at a temperature of 20° C. to 1,000 to 125,000 mPa·s.

If the mixing ratio (the mass of the first liquid concentrate composition: the mass of the second liquid concentrate composition) is out of the above-described range, the amount of the first liquid concentrate composition discharged from the first liquid concentrate filling space is significantly different from the amount of the second liquid concentrate composition discharged from the second liquid concentrate filling space. Therefore, a mixed discharge material (specifically, the first liquid concentrate composition and the second liquid concentrate composition) may fail to have desired functions and may fail to provide comfort during use when it is applied to the human body.

The two-liquid mixing-type aerosol product of the present invention described above is produced by filling the first liquid concentrate filling space and the second liquid concentrate filling space in the double-structure container with the first liquid concentrate composition and the second liquid concentrate composition, respectively, and filling the propellant filling space with the propellant.

The two-liquid mixing-type aerosol product of the present invention has a double-structure container including a discharging mechanism for simultaneously discharging the contents filled in two liquid concentrate filling spaces. One of two liquid concentrate filling spaces is filled with the first liquid concentrate composition having a particular viscosity, whereas the other is filled with the second liquid concentrate composition having a particular viscosity.

Therefore, the first liquid concentrate composition and the second liquid concentrate composition both have a large degree of freedom in formulation design, and high formulation stability is obtained.

In addition, the first liquid concentrate composition and the second liquid concentrate composition can be simultaneously discharged from two liquid concentrate filling spaces in the double-structure container in suitable amounts (specifically, in the same amount), respectively. Even when the first liquid concentrate composition and the second liquid concentrate composition have a high viscosity, the first liquid concentrate composition and the second liquid concentrate composition can always be mixed at a constant quantitative ratio, so that there is no possibility that the amount of one liquid concentrate composition discharged is much larger than the amount of another liquid concentrate composition discharged. As a result, a highly viscous discharge material having desired functions and formed by a combination of the first liquid concentrate composition and the second liquid concentrate composition having different properties can always be obtained when the first liquid concentrate composition and the second liquid concentrate composition are discharged by simply operating the discharging mechanism, specifically, for example, only depressing the actuator once (one push).

Moreover, the long-term storage stability can be obtained because neither the first liquid concentrate composition nor the second liquid concentrate composition is exposed to the air outside the container during application.

The two-liquid mixing-type aerosol product of the present invention has high storage stability and can easily form a highly viscous discharge material with high functionality.

In the two-liquid mixing-type aerosol product of the present invention, as shown in the examples (1-1) to (5-8) described above, active ingredients that are considered difficult to use in combination in the same stock solution from the viewpoint of formulation stability (for example, formulation stability of active ingredients, and formulation stability of a base) and the like can be stored in combination without any undesirable effects and can be used together. Specifically, in the examples (1-1) to (2-5) and the examples (5-1) to (5-8), two liquid concentrate compositions have a different formulation. To obtain desired effects, these liquid concentrate compositions cannot be stored as a mixture during storage from the viewpoint of formulation design. However, these two liquid concentrate compositions can be filled and stored in one double-structure container. In the examples (3-1) and (4-1), two liquid concentrate compositions each contain a reactive active ingredient, and thus these two liquid concentrate compositions cannot be stored as a mixture during storage. However, these two liquid concentrate compositions can be filled and stored in one double-structure container.

In the two-liquid mixing-type aerosol product of the present invention, a non-flammable compressed gas is used as a propellant for the first liquid concentrate composition and the second liquid concentrate composition. The use of the non-flammable compressed gas provides high safety irrespective of the operation environment and eliminates the risk of an explosion accident in discarding the double-structure container.

The two-liquid mixing-type aerosol product of the present invention can be used in various applications, such as daily necessaries, food, and products for the human body such as cosmetic preparations.

Specifically, the two-liquid mixing-type aerosol product of the present invention can be used as, for example, hair styling agents, hair treatment agents, hair dyes, hair growth agents, massaging agents, skin protective agents, moisturizers, makeup bases, whitening agents, sunscreens, facial washes, facial masks, and depilatory agents.

EXAMPLES

Examples of the present invention will be described below, but the present invention is not limited by these.

Example 1: Production of Two-Liquid Mixing-Type Aerosol Product for Hair Treatment Agent Preparation of First Liquid Concentrate Composition:
A first liquid concentrate composition was prepared by mixing the components described below.
The viscosity of the obtained first liquid concentrate composition at a temperature of 20° C. was measured using a BM-type rotary viscometer (rotor No. 4, 12 rpm, after 1 minute) and found to be 10,000 mPa·s.
Constituents of First Liquid Concentrate Composition:
Purified water: 84.6% by mass
Propylene glycol: 5.0% by mass
Cetearyl alcohol: 3.0% by mass
Dimethicone: 3.00% by mass
Phenyl trimethicone: 3.0% by mass
Behentrimonium chloride: 0.5% by mass
Sorbeth-60 tetraoleate: 0.3% by mass
Methylparaben: 0.3% by mass
Hydrolyzed collagen: 0.1% by mass
Keratin: 0.1% by mass
Flavor: 0.1% by mass
Total: 100.0% by mass
Preparation of Second Liquid Concentrate Composition:
A second liquid concentrate composition was prepared by mixing the components described below.
The viscosity of the obtained second liquid concentrate composition at a temperature of 20° C. was measured using a BM-type rotary viscometer (rotor No. 4, 12 rpm, after 1 minute) and found to be 13,000 mPa·s.
Constituents of Second Liquid Concentrate Composition:
Light liquid isoparaffin: 93.0% by mass
Dextrin palmitate/ethylhexanoate: 5.0% by mass
Jojoba oil: 1.0% by mass
Olive oil: 1.0% by mass
Total: 100.0% by mass
Production of Two-Liquid Mixing-Type Aerosol Product:
A two-liquid mixing-type aerosol product for use as a hair treatment agent was produced by: preparing a double-structure container having the structure illustrated in FIG. 1 and FIG. 2; filling a first liquid concentrate filling space (first inner bag) in the double-structure container with the first liquid concentrate composition; filling a second liquid concentrate filling space (second inner bag) with the second liquid concentrate composition; and filling a propellant filling space with nitrogen gas as a propellant such that the product inner pressure in the double-structure container was 0.7 MPa at 25° C. In this two-liquid mixing-type aerosol product, the first liquid concentrate composition is a water-based hair treatment liquid cosmetic formulation. The second liquid concentrate composition is an oil-based hair treatment liquid cosmetic formulation.

Example 2: Production of Two-Liquid Mixing-Type Aerosol Product for Hair Styling Agent Preparation of First Liquid Concentrate Composition:
A first liquid concentrate composition was prepared by mixing the components described below.
The viscosity of the obtained first liquid concentrate composition at a temperature of 20° C. was measured using a BM-type rotary viscometer (rotor No. 4, 6 rpm, after 1 minute) and found to be 50,000 mPa·s.

Constituents of First Liquid Concentrate Composition:
Glyceryl stearate (SE): 10.0% by mass
Polyoxyethylene hydrogenated castor oil (PEG-60 hydrogenated castor oil): 3.0% by mass
Stearyl alcohol: 3.0% by mass
Cetyl palmitate: 3.0% by mass
Ceresin: 1.5% by mass
Octyl palmitate: 2.5% by mass
Olive squalane: 10.0% by mass
Trioctanoin: 5.0% by mass
Dimethicone: 1.0% by mass
Purified water: 50.8% by mass
Glycerol: 3.0% by mass
1,3-Butylene glycol: 7.0% by mass
Methylparaben: 0.2% by mass
Total: 100.0% by mass Preparation of Second Liquid Concentrate Composition:
A second liquid concentrate composition was prepared by mixing the components described below.

The viscosity of the obtained second liquid concentrate composition at a temperature of 20° C. was measured using a BM-type rotary viscometer (rotor No. 4, 12 rpm, after 1 minute) and found to be 35,000 mPa·s.

Constituents of Second Liquid Concentrate Composition:
Purified water: 80.1% by mass
Ethanol: 10.0% by mass
Vinyl acetate-vinylpyrrolidone copolymer: 8.0% by mass
Triethanolamine: 0.6% by mass
Carboxyvinyl polymer: 0.6% by mass
1,3-Butylene glycol: 0.5% by mass
Methylparaben: 0.2% by mass
Total: 100.0% by mass Production of Two-Liquid Mixing-Type Aerosol Product:
A two-liquid mixing-type aerosol product for use as a hair styling agent was produced by: preparing a double-structure container having the structure illustrated in FIG. 1 and FIG. 2; filling a first liquid concentrate filling space (first inner bag) in the double-structure container with the first liquid concentrate composition; filling a second liquid concentrate filling space (second inner bag) with the second liquid concentrate composition; and filling a propellant filling space with nitrogen gas as a propellant such that the product inner pressure in the double-structure container was 0.7 MPa at 25° C. In this two-liquid mixing-type aerosol product, the first liquid concentrate composition is a wax-type hair treatment cosmetic formulation. The second liquid concentrate composition is a jelly-type hair styling cosmetic formulation.

The two-liquid mixing-type aerosol products in Example 1 and Example 2 are found to have favorable functions attributed to the first liquid concentrate composition and the second liquid concentrate composition as the feeling during use has been examined immediately after production.

It is also found that, even after long-term storage in an environment at a temperature of 45° C. for one month, the two-liquid mixing-type aerosol products in Example 1 and Example 2 exert favorable functions and provide comfort during use similarly to those obtained immediately after production.

REFERENCE SIGNS LIST 10 double-structure container
11 pressure resistant container
12 aerosol valve
13A first housing
13B second housing
14A first stem
14B second stem
15A first inner bag
15B second inner bag
16A first dip tube
16B second dip tube
21 actuator
22A first actuator passage
22B second actuator passage
23 discharge space
24 discharge port
31 actuator
32A first actuator passage
32B second actuator passage
34A first discharge port
34B second discharge port

The invention claimed is:

1. A two-liquid mixing-type aerosol product comprising:
a double-structure container including a propellant filling space and two independent liquid concentrate filling spaces and having a discharging mechanism for simultaneously discharging contents filled in the two liquid concentrate filling spaces, wherein:
the propellant filling space in the double-structure container is filled with a propellant comprising a compressed gas,
a first liquid concentrate filling space in the double-structure container is filled with a first liquid concentrate composition, and a second liquid concentrate filling space in the double-structure container is filled with a second liquid concentrate composition,
the first liquid concentrate composition and the second liquid concentrate composition have different properties,
the first liquid concentrate composition comprises an oil-in-water emulsion composition, and the second liquid concentrate composition comprises a water-in-oil emulsion composition, and
the first liquid concentrate composition and the second liquid concentrate composition each have a viscosity of greater than 50,000 mPa·s and not exceeding 125,000 mPa·s at a temperature of 20° C.

2. The two-liquid mixing-type aerosol product according to claim 1, wherein
the first liquid concentrate composition comprises a water-based liquid composition containing a water-soluble component in a medium comprising water, and
the second liquid concentrate composition comprises an oil-based liquid composition containing an oil-soluble component in a medium comprising a liquid oil or fat immiscible with water.

3. The two-liquid mixing-type aerosol product according to claim 1, wherein
the first liquid concentrate composition comprises an alkaline liquid composition comprising an alkaline component, and
the second liquid concentrate composition comprises an acidic liquid composition comprising an acidic component.

4. The two-liquid mixing-type aerosol product according to claim 1, wherein
the first liquid concentrate composition comprises a liquid reducing agent composition comprising a reducing agent, and the second liquid concentrate composition comprises a liquid oxidizing agent composition comprising an oxidizing agent.

5. The two-liquid mixing-type aerosol product according to claim 1, wherein
a mixing ratio of a first mass of the first liquid concentrate composition to a second mass of the second liquid concentrate composition discharged from the discharging mechanism is from 0.8:1.2 to 1.2:0.8.

* * * * *